(12) United States Patent
Brase

(10) Patent No.: US 9,744,367 B2
(45) Date of Patent: Aug. 29, 2017

(54) FEED THROUGH INTERCONNECT ASSEMBLY FOR AN IMPLANTABLE STIMULATION SYSTEM AND METHODS OF MAKING AND USING

(75) Inventor: Randall Lee Brase, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 432 days.

(21) Appl. No.: 13/525,049

(22) Filed: Jun. 15, 2012

(65) Prior Publication Data

US 2012/0259397 A1   Oct. 11, 2012

Related U.S. Application Data

(62) Division of application No. 11/532,844, filed on Sep. 18, 2006, now Pat. No. 8,224,450.

(51) Int. Cl.
*A61N 1/36*   (2006.01)
*A61N 1/375*  (2006.01)

(52) U.S. Cl.
CPC .. *A61N 1/3754* (2013.01); *H01L 2924/01079* (2013.01); *Y10T 29/49169* (2015.01); *Y10T 29/49174* (2015.01)

(58) Field of Classification Search
CPC ..... A61N 1/3754; A61N 1/3752; A61N 1/375
USPC ................................. 607/5, 36, 37
See application file for complete search history.

(56) References Cited

U.S. PATENT DOCUMENTS

| | | | |
|---|---|---|---|
| 3,601,747 A | 8/1971 | Prall et al. | |
| 3,718,142 A | 2/1973 | Muller | |
| 3,771,106 A | 11/1973 | Matsumoto et al. | |
| 4,003,616 A * | 1/1977 | Springer | 439/23 |
| 4,364,625 A | 12/1982 | Baker et al. | |
| 4,367,907 A | 1/1983 | Buck | |

(Continued)

FOREIGN PATENT DOCUMENTS

| | | |
|---|---|---|
| WO | WO-98/37926 | 9/1998 |
| WO | WO-98/43700 | 10/1998 |
| WO | WO-98/47301 | 10/1998 |

OTHER PUBLICATIONS

U.S. Appl. No. 13/525,063, Official Communication mailed Sep. 27, 2012.

(Continued)

*Primary Examiner* — Michael D Abreu
(74) *Attorney, Agent, or Firm* — Lowe Graham Jones PLLC; Bruce E. Black

(57) ABSTRACT

A stimulation system includes an implantable pulse generator having a sealed chamber and an electronic subassembly disposed in the sealed chamber. Feed through pins are coupled to the electronic subassembly and extend out of the sealed chamber. Feed through interconnects are coupled to the electronic subassembly via the feed through pins. At least one tab is disposed on at least one feed through interconnect. The tab(s) are configured and arranged to flex away from the feed through interconnect and against a side of the feed through pin.

A feed through interconnect assembly includes an assembly frame; feed through interconnects extending from the assembly frame; a first contact pad and a second contact pad disposed on at least one of the feed through interconnects; and a tab formed on a first contact pad of at least one of the feed through interconnects.

17 Claims, 4 Drawing Sheets

(56) References Cited

U.S. PATENT DOCUMENTS

| | | | |
|---|---|---|---|
| 4,695,116 A | 9/1987 | Bailey et al. | |
| 4,695,117 A | 9/1987 | Kysiak | |
| 4,712,557 A | 12/1987 | Harris | |
| 4,867,708 A | 9/1989 | Iizuka et al. | |
| 5,086,773 A * | 2/1992 | Ware | 607/2 |
| 5,193,539 A | 3/1993 | Schulman et al. | |
| 5,193,540 A | 3/1993 | Schulman et al. | |
| 5,312,439 A | 5/1994 | Loeb | |
| 5,435,731 A | 7/1995 | Kang et al. | |
| 5,556,421 A | 9/1996 | Prutchi et al. | |
| 6,024,704 A * | 2/2000 | Meador | A61B 5/0215 128/899 |
| 6,051,017 A | 4/2000 | Loeb et al. | |
| 6,181,969 B1 | 1/2001 | Gord | |
| 6,516,227 B1 | 2/2003 | Meadows et al. | |
| 6,604,283 B1 | 8/2003 | Kuzma | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,757,970 B1 | 7/2004 | Kuzma et al. | |
| 6,899,976 B2 | 5/2005 | Larson et al. | |
| 6,912,781 B2 | 7/2005 | Morrison et al. | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,966,070 B2 | 6/2011 | Taylor et al. | |
| 7,974,706 B2 | 7/2011 | Moffitt et al. | |
| 8,224,450 B2 | 7/2012 | Brase | |
| 2001/0019926 A1 | 9/2001 | Natali | |
| 2006/0167522 A1* | 7/2006 | Malinowski | A61N 1/3752 607/37 |
| 2007/0150036 A1 | 6/2007 | Anderson | |
| 2010/0261362 A1* | 10/2010 | Boyd | A61N 1/375 439/271 |

OTHER PUBLICATIONS

U.S. Appl. No. 13/525,063, Official Communication mailed Apr. 22, 2013.

U.S. Appl. No. 11/532,844, Official Communication mailed Sep. 4, 2008.

U.S. Appl. No. 11/532,844, Official Communication mailed Feb. 19, 2009.

U.S. Appl. No. 11/532,844, Official Communication mailed Jun. 4, 2009.

U.S. Appl. No. 11/532,844, Official Communication mailed Jan. 6, 2010.

U.S. Appl. No. 11/532,844, Official Communication mailed Oct. 27, 2010.

* cited by examiner

FEED THROUGH INTERCONNECT ASSEMBLY FOR AN IMPLANTABLE STIMULATION SYSTEM AND METHODS OF MAKING AND USING

CROSS-REFERENCE TO RELATED APPLICATIONS

This utility patent application is a divisional of U.S. patent application Ser. No. 11/532,844, filed Sep. 18, 2006, and is incorporated herein by reference.

FIELD OF THE INVENTION

The invention is directed to implantable stimulation systems. In addition, the invention is directed to implantable stimulation systems having feed through interconnects, and methods of making the devices.

BACKGROUND OF THE INVENTION

Stimulation systems have been developed to provide therapy for a variety of disorders, as well as other treatments. For example, stimulation systems can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Stimulation systems, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. Other stimulators, such as the Precision® rechargeable stimulator, in combination with linear/percutaneous leads or paddle type leads are used to stimulate the spinal cord for treating intractable chronic pain. It is preferable that the electronic circuitry and power source be held within the housing in a hermetically-sealed environment for the protection of the user and the protection of the circuitry and power source. Once implanted, it is often preferable that the stimulation system can be controlled and/or that the electrical source can be charged without removing the stimulation system from the implanted environment.

BRIEF SUMMARY OF THE INVENTION

One embodiment is a stimulation system that includes an implantable pulse generator having a sealed chamber and an electronic subassembly disposed in the sealed chamber. Feed through pins are coupled to the electronic subassembly and extend out of the sealed chamber. Feed through interconnects are coupled to the electronic subassembly via the feed through pins. At least one tab is disposed on at least one feed through interconnect. The tab(s) are configured and arranged to flex away from the feed through interconnect and against a side of the feed through pin.

Another embodiment is a feed through interconnect assembly that includes an assembly frame; feed through interconnects extending from the assembly frame; a first contact pad and a second contact pad disposed on at least one of the feed through interconnects; and a tab formed on a first contact pad of at least one of the feed through interconnects.

Yet another embodiment is a method of making a stimulation device by coupling a feed through interconnect assembly to a lead connector. The feed through interconnect assembly has an assembly frame, feed through interconnects extending from the assembly frame, a first contact pad and a second contact pad disposed on at least one of the feed through interconnects, and a tab formed on a first contact pad of at least one of the feed through interconnects. The feed through interconnect assembly is coupled to an implantable pulse generator which has a sealed chamber, an electronic subassembly disposed in the sealed chamber, and feed through pins coupled to the electronic subassembly and extending through the sealed chamber.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION OF THE INVENTION

Figure 1:
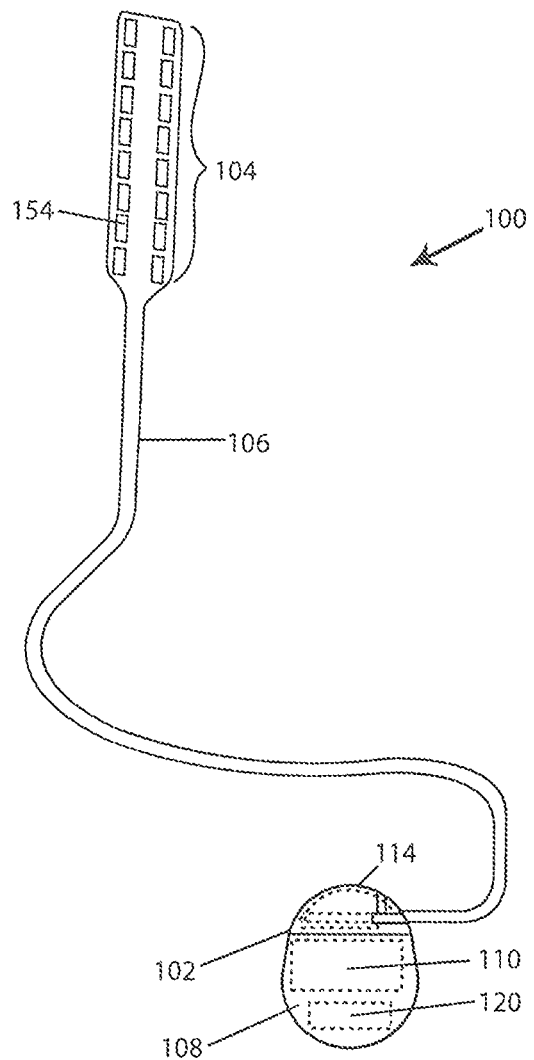
FIG. 1 is a schematic perspective view of one embodiment of a stimulation system, according to the invention.

The invention is directed to implantable stimulation systems. In addition, the invention is directed to implantable stimulation systems having feed through interconnects, and methods of making the devices.

Examples of suitable stimulators and stimulation systems can be found in, for example, U.S. Pat. Nos. 6,609,032; 6,181,969; 6,516,227; 6,609,029; 6,741,892; 7,244,150; 7,672,734; and 7,974,706; and U.S. Patent Application Publication No. 2007/0150036, all of which are incorporated herein by reference.

A stimulation system can include an electrode lead coupled to an implantable pulse generator. The implantable pulse generator may include a housing and an electronic subassembly disposed (and, preferably, hermitically sealed) within the housing. The implantable pulse generator may further include feed through pins that are coupled to the electronic subassembly and that extend through the housing. The lead may have several lead contacts that connect to individual feed through pins on the implantable pulse generator. For example, the lead may have a lead contact for each electrode. The lead contacts may connect to the feed through pins on the implantable pulse generator via a lead connector.

A wire may be used to couple the lead connector to the feed through pins on the implantable pulse generator. However, using a wire can present manufacturing complications such as maintaining the position of the wire while attaching the wire to the feed through pins and/or the lead connector. In addition, using a wire may present failure points at the weld junctions of the wire to the feed through pins as well as at the weld junction of the wire to the lead connector. Furthermore, manufacturing constraints can impose restrictions on the diameter of the wire. Restricting the diameter of the wire may affect the fatigue life of the wire, resulting in premature failure and shortening of the device's longevity.

Longer feed through pins that directly connect to the contacts of the lead connector may also be used. However, a longer feed through pin may result in additional force being applied directly to the feed through pin. This additional force may also damage seals that may be present in the implantable pulse generator.

A feed through interconnect assembly can be used to couple the implantable pulse generator feed through pins to the lead connector. The feed through interconnect assembly can include, for example, an assembly frame, feed through interconnects extending from the assembly frame, contact pads disposed on the feed through interconnects, and tabs formed on the contact pads of the feed through interconnects. One or more optional indexing holes may be located on the assembly frame. In addition, one or more optional braces may couple the assembly frame to the feed through interconnects extending from the assembly frame.

A feed through interconnect assembly can be used to make a stimulation system. The feed through interconnect assembly may be coupled to at least one feed through pin of an implantable pulse generator. The feed through interconnect assembly may further be coupled to at least one lead connector. Before, during, or after the coupling of feed through interconnect assembly to the feed through pin(s) of the implantable pulse generator and the lead connector(s), some components of the feed through interconnect assembly may be removed. For example, the assembly frame may be removable. Alternatively, or additionally, braces that couple the feed through interconnects to the assembly frame may be removable.

FIG. 1 illustrates schematically one embodiment of a stimulation system 100. The stimulation system includes an implantable pulse generator 102 and a lead 106. A distal portion of the lead body contains one or more electrodes (e.g., an electrode array 104). It will be understood that the stimulation system can include more or different components and can have a variety of different configurations including those configurations disclosed in the stimulation system references cited herein. The stimulation system or components of the stimulation system, including the lead 106 and the implantable pulse generator 102, are implanted into the body. The implantable pulse generator 102 typically includes a housing 114 with an electronic subassembly 110 and, in at least some embodiments, a power source 120, disposed within a sealed chamber 108 in the housing 114.

Figure 2:
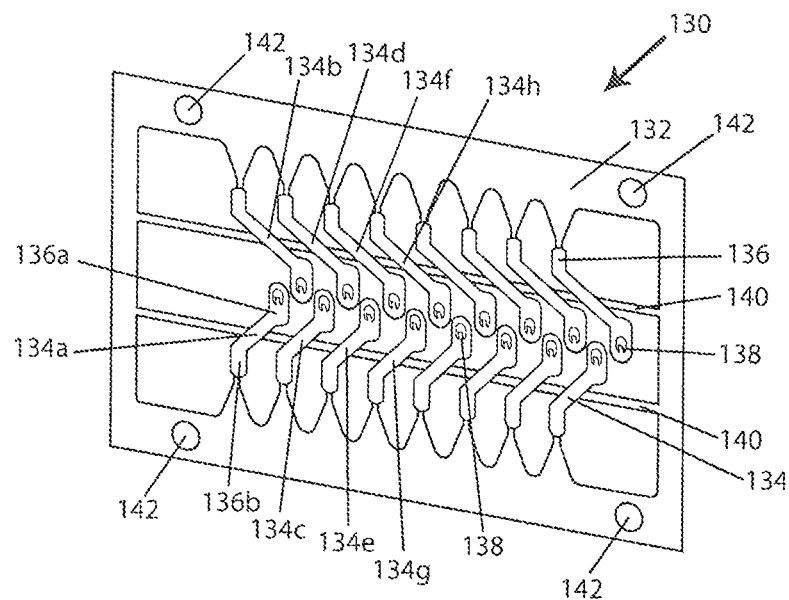
FIG. 2 is a schematic perspective view of one embodiment of a feed through interconnect assembly, according to the invention.
Figure 3:
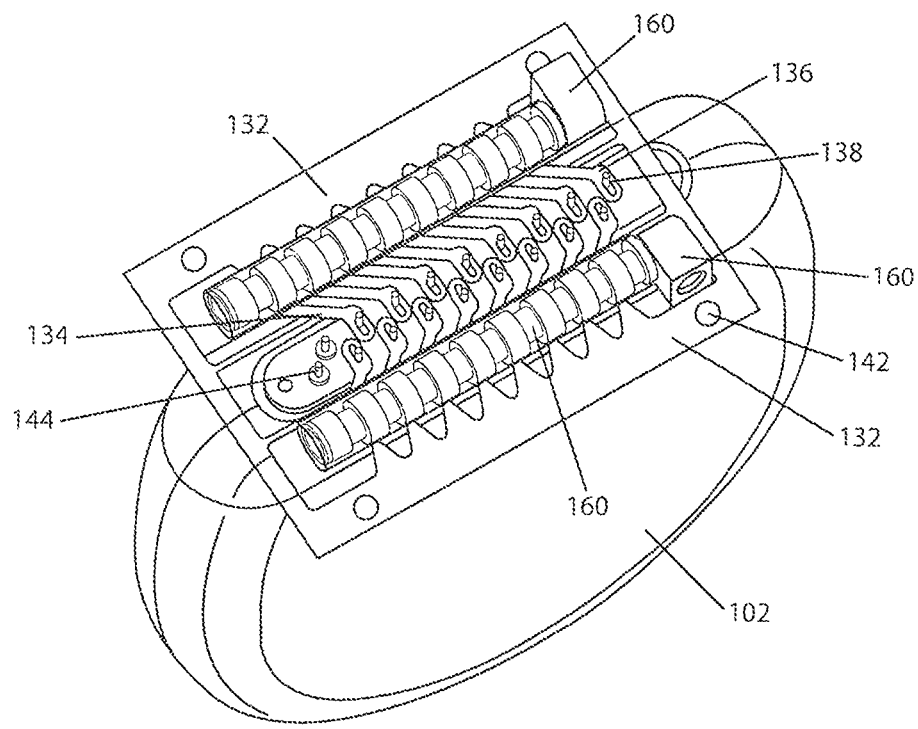
FIG. 3 is a schematic perspective view of the feed through interconnect assembly of FIG. 2 coupled to an implantable pulse generator and lead connectors, according to the invention.

One embodiment of a feed through interconnect assembly 130 is illustrated in FIG. 2. A feed through interconnect assembly 130 may be used to couple the lead connector(s) 160 to the feed through pin(s) 144 of the implantable pulse generator 102, as illustrated in FIG. 3. A feed through interconnect assembly 130 may include an assembly frame 132, feed through interconnects 134 extending from the assembly frame 132, contact pads 136 disposed on the feed through interconnects 134, and tabs 138 formed on the contact pads 136 of the feed through interconnects 134. One or more optional indexing holes 142 may be located on the assembly frame 132. In addition, one or more optional braces 140 may couple the assembly frame 132 to the feed through interconnects 134 extending from the assembly frame 132.

An assembly frame 132 can be made of any material including, for example, stainless steel materials (e.g., 316L and MP35N), platinum, platinum/iridium, titanium, other metals and alloys, polymers, and the like. The assembly frame may have any shape including, for example, a square, rectangular, circular or elliptical shape. Typically, the assembly frame 132 is removable from the feed through interconnects 134. For example, the assembly frame 132 may be removed from the feed through interconnect assembly 130 either before, during, or after the feed through interconnect assembly 130 is coupled to the lead connector(s) 160 or the feed through pins 144 of the implantable pulse generator 102 (see FIG. 3).

One or more indexing holes 142 may be located on the assembly frame 132. The indexing holes 142 may have any shape. There may be any number of indexing holes including, for example, zero, one, two, three, four, five, six, seven, eight, nine, or ten. As will be recognized, other numbers of indexing holes 142 are also possible. The indexing hole(s) may be located anywhere on the assembly frame 132. Preferably, the indexing holes 142 are shaped and located such that the indexing holes aid in positioning the feed through interconnect assembly 130 with respect to the implantable pulse generator 102 during the manufacturing process.

The feed through interconnects 134 can extend from the assembly frame 132 in any desired arrangement. For example, the feed through interconnects 134 may extend from at least one side of the assembly frame 132 towards the opposite side of the assembly frame as illustrated, for example, in FIG. 2. The feed through interconnects 134 may extend from the assembly frame 132 either below, above or in the plane of the assembly frame 132.

Feed through interconnects 134 are made of any conductive material that is preferably biocompatible. Suitable materials for feed through interconnects 134 include, for example, stainless steel materials (e.g., 316L and MP35N), platinum, platinum/iridium, titanium, other metals and alloys, polymers, and the like. The feed through interconnects 134 are preferably made of a material that allows the feed through interconnects 134 to be bent or otherwise re-positioned. Feed through interconnects 134 may have any shape. Preferably, feed through interconnects 134 have a shape that allows the feed through interconnects 134 to couple the feed through pins 144 of the implantable pulse generator 102 to the lead connector(s) 160.

There may be any number of feed through interconnects 134 including, for example, two, three, four, five, six, seven, eight, nine, ten, eleven, twelve, thirteen, fourteen, fifteen, sixteen, seventeen, eighteen, nineteen, twenty, twenty-one, or twenty-two feed through interconnects 134. As will be recognized, other numbers of feed through interconnects 134 are also possible. Preferably, the number of feed through interconnects 134 is equal to the number of feed through pins 144 (see FIG. 3) of the implantable pulse generator 102.

In at least some embodiments, the feed through interconnects 134 are spaced apart at substantially uniform distances. For example, the distance between the feed through interconnects 134 may vary by no more than about 2.5 mm.

Feed through interconnects 134 may extend from more than one side of the assembly frame 132. For example, feed through interconnects 134 may extend from two opposing sides of the assembly frame 132 as illustrated, for example, in FIG. 2. Feed through interconnects 134 may be interleaved. For example, the feed through interconnects 134 extending from the assembly frame 132 may alternate between feed through interconnects 134 extending from a first side of the assembly frame 132 and feed through interconnects 134 extending from a second side of the assembly frame 132. One embodiment of interleaving feed through interconnects 134 is illustrated in FIG. 2. In FIG. 2, the feed through interconnects 134 alternate between feed through interconnects 134a, 134c, 134e, 134g that extend from a first side of the assembly frame 132 and feed through interconnects 134b, 134d, 134f, and 134h that extend from a second side of the assembly frame 132. As will be recognized, in other embodiments feed through interconnects 134 may be interleaved, such that two, three, four or more feed through interconnects 134 extend from a first side of the assembly frame 132 before alternating to feed through interconnects 134 extending from a second side of the assembly frame 132.

Contact pads 136 are disposed on the feed through interconnects 134. The contact pads 136 may be made of any conductive material that is preferably biocompatible including, for example, stainless steel materials (e.g., 316L and MP35N), platinum, platinum/iridium, titanium, other metals and alloys, polymers, and the like. The contact pads 136 may have any shape including, for example, a square, circular, elliptical, or rectangular shape. The contact pads 136 may have a width that is smaller, equal to, or greater than the width of the feed through interconnects 134.

One or two contact pads may be disposed on a feed through interconnect 134. Preferably, two contact pads 136 are disposed on each feed through interconnect 134 as illustrated in FIG. 2. For example, a first contact pad 136 located on the distal end of the feed through interconnect 134 can facilitate coupling of the feed through interconnect 134 with the feed through pin 144 of the implantable pulse generator 102, while a second contact pad 136 located on the proximal end of the feed through interconnect 134 can facilitate coupling of the feed through interconnect 134 with the lead connector 160. In one embodiment, a first contact pad 136a located at a distal end of feed through interconnect 134a and a second contact pad 136b located at a proximal end of feed through interconnect 134a are illustrated in FIG. 2.

The feed through interconnects 134 may also include one or more tabs 138. Preferably, the number of tabs 138 is equal to the number of feed through pins 144 (see FIG. 3) of the implantable pulse generator 102. Preferably, the tabs 138 are disposed on at least one contact pad 136 of a feed through interconnect 134. In at least some embodiments, one tab 138 is disposed on a first contact pad 136 for each feed through interconnect 134 as illustrated, for example, in FIG. 2.

Preferably, the tab 138 is formed to allow the tab 138 to flex and distribute any forces transmitted to the feed through pin(s) 144 (see FIG. 3). Preferably, the tabs 138 are configured and arranged such that the tabs 138 flex away from the contact pads 136 and against a side of the feed through pin 144 (see FIGS. 3 and 4). Preferably, the tabs 138 are formed such that the tabs 138 have contact with the feed through pins 144 when the feed through interconnects 134 are attached.

The feed through interconnect assembly 130 may include at least one brace 140. In some embodiments, braces 140 are illustrated schematically in FIG. 2. The feed through interconnect assembly 130 may include any number of braces 140 including, for example, zero, one, two, three, four, five, six, seven, eight, nine, or ten braces 140. As will be recognized, other numbers of braces 140 are also possible. The brace(s) 140 may be made of any material including, for example, stainless steel materials (e.g., 316L and MP35N), platinum, platinum/iridium, titanium, other metals and alloys, polymers, and the like. For ease of manufacture, the assembly frame 132, braces 140 and feed through interconnects can be formed of the same material.

A brace 140 is preferably located such that it couples at least one feed through interconnect 134 to the assembly frame 132. For example, a brace 140 may couple at least one feed through interconnect 134 extending from a first side of the assembly frame 132 to the assembly frame 132 as illustrated in FIG. 2. Additionally or alternatively, a brace 140 may couple at least one feed through interconnect 134 extending from a second side of the assembly frame 132 to the assembly frame (see FIG. 2). Preferably, the brace(s) 140 is capable of being removed from the feed through interconnect assembly 130 after the feed through interconnect assembly 130 has been used to couple the feed through pins 144 of the implantable pulse generator 102 to the lead connector 160.

The feed through interconnect assembly 130 may be made in any manner including, for example, molding, stamping, or otherwise cutting the assembly from a sheet of material. The feed through assembly 130 may optionally be coated with a coating such as, for example, silicone, paralene, Teflon (ETFE, PFA, PTFE) or Kapton. The coating may optionally provide electrical isolation between, for example, adjacent connector contacts 170 or adjacent feed through pins 144.

Turning to FIG. 3, a method of making a stimulation device includes coupling a feed through interconnect assembly 130 to an implantable pulse generator 102. A method of making a stimulation device also includes coupling a feed through interconnect assembly 130 to at least one lead connector 160.

Figure 4:
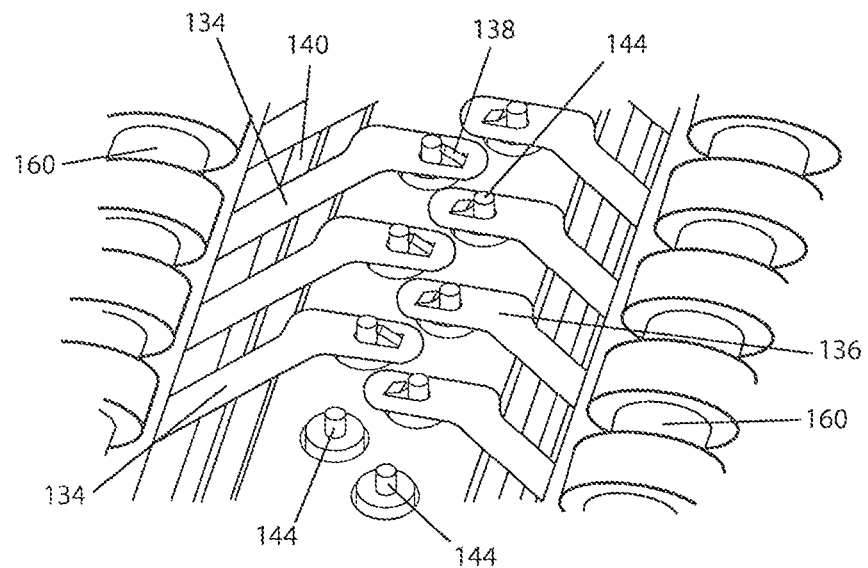
FIG. 4 is a schematic close-up perspective view of a portion of the feed through interconnect assembly of FIG. 3 coupled to the implantable pulse generator.

As set forth above, an implantable pulse generator 102 may include a sealed chamber 108 (see FIG. 1). An electronic subassembly 110 may be disposed in the sealed chamber 108 of the implantable pulse generator 102. The implantable pulse generator 102 may also include feed through pins 144 as illustrated in FIGS. 3 and 4. Preferably, the feed through pins 144 are coupled to the electronic subassembly 110 and extend through the housing 114 to the sealed chamber 108.

Figure 5:
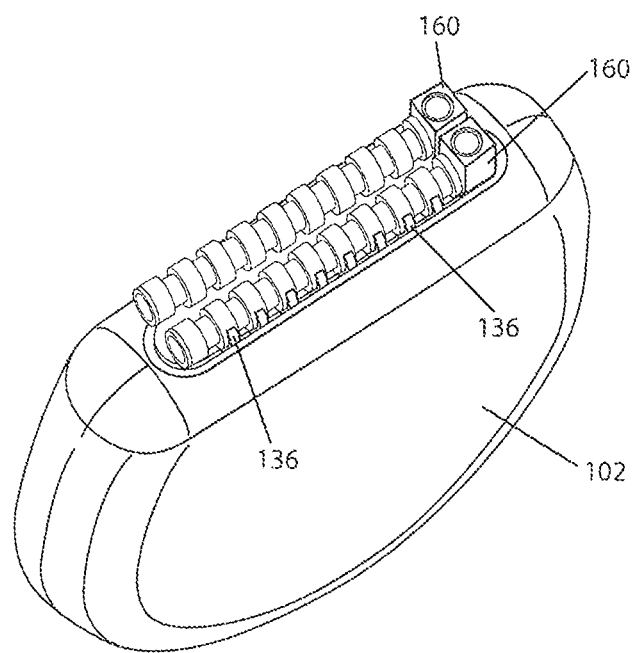
FIG. 5 is a schematic perspective view of one embodiment of an implantable pulse generator coupled to lead connectors via feed through interconnects, according to the invention.

Feed through pins 144 may be made of any conductive material that is preferably biocompatible. Suitable materials for feed through pins 144 include, for example, metals, alloys, conductive polymers, and the like. There may be any number of feed through pins 144 including one, two, three, four, five, six, seven, eight, nine, ten, eleven, twelve, thirteen, fourteen, fifteen, sixteen, seventeen, eighteen, nineteen, twenty, twenty-one, twenty-two or more feed through pins 144. As will be recognized, other numbers of feed through pins 144 are also possible. Preferably, the number of feed through pins 144 is equal to the number of electrodes on the electrode array 104 (see FIGS. 3 and 5).

A first contact pad 136 disposed on each feed through interconnect 134 may be coupled to each feed through pin 144 extending from the sealed chamber 108 of the implantable pulse generator 102. Even more preferably, the tabs 138 formed on the contact pads 136 are coupled to the feed through pins 144 of the implantable pulse generator 102. The tabs 138 may be coupled to the feed through pins 144 in any manner including, for example, by friction fit and/or by soldering, welding, and the like. In some embodiments, the tabs 138 could also be coupled to the feed through pins 144 by the contact force due to flexing.

The feed through interconnect assembly 130 is coupled to at least one lead connector 160, as illustrated in FIG. 3. A lead connector 160 is preferably configured and arranged to receive the proximal portion of a lead. A lead connector 160 may be made of any biocompatible material including, for example, silicone and polyurethane. One embodiment of a method of making a lead connector 160 is disclosed in U.S. Pat. No. 7,244,150, incorporated herein by reference.

The lead connector 160 includes connector contacts 170. The connector contacts 170 may be made of any conductive material that is preferably biocompatible including, for example, metals, alloys, conductive polymers, and the like. There may be any number of connector contacts 170 including, for example, one, two, three, four, five, six, seven, eight, nine, ten, eleven, twelve, thirteen, fourteen, fifteen, sixteen, seventeen, eighteen, nineteen, twenty, twenty-one, twenty-two, or more connector contacts 170. As will be recognized, other numbers of connector contacts 170 are also possible. Preferably, the number of connector contacts 170 is equal to the number of feed through pins 144 of the implantable pulse generator 102.

The feed through interconnect assembly 130 can be coupled to the lead connector 160 in any manner, including soldering, welding and the like. Preferably, the feed through interconnect assembly 130 is coupled to the connector contacts 170 of the lead connector 160. More preferably, at least one feed through interconnect 134 is coupled to at least one connector contact 170. More preferably, at least one contact pad 136 disposed on at least one feed through interconnect 134 is coupled to at least one connector contact 170.

The position of the lead connector 160 may be altered after the lead connector 160 is coupled to the feed through interconnect assembly 130. For example, as illustrated in FIG. 3, the lead connector 160 may initially be coupled to the feed through interconnect assembly 130 such that the position of the lead connector 160 does not substantially interfere with the coupling of the feed through interconnect assembly 130 to the feed through pins 144 of the implantable pulse generator 102. Then, after the feed through interconnect assembly 130 is coupled to the feed through pins 144, the position of the lead connector 160 may be altered as illustrated, for example, in FIG. 5. Feed through interconnects 134 that are flexible may be used to facilitate re-positioning of the lead connector 160. For example, flexible feed through interconnects 134 may wrap around at least a portion of the circumference of the lead connector 160.

In some embodiments, components of the feed through interconnect assembly 130 may be removed before, during, or after coupling the feed through interconnect assembly 130 to the implantable pulse generator 102 and/or to the lead connector 160. For example, the assembly frame 132 may be removed from the feed through interconnect assembly 130 before, during, or after coupling the feed through interconnect assembly 130 to the implantable pulse generator 102 and/or to the lead connector 160. In another example, at least one brace 140 may be removed from the feed through interconnect assembly 130 before, during, or after coupling the feed through interconnect assembly 130 to the implantable pulse generator and/or to the lead connector 160.

Returning to FIG. 1, the housing is preferably resistant to moisture penetration into the chamber containing the electronic subassembly and power source. In some embodiments, water may diffuse through the housing. Preferably, the diffused water is relatively pure, without substantial ionic content, as deionized water is relatively non-conductive.

The housing 114 may be made of any biocompatible material including, for example, glass, ceramics, metals, and polymers. In one embodiment, the housing 114 of the implantable pulse generator is formed of a plastic material that resists the transport of moisture into the interior of the housing and is sufficiently sturdy to protect the components on the interior of the housing from damage under expected usage conditions. Preferably, the material of the plastic housing is a hydrophobic polymer material. The housing 114 may include additives such as, for example, fillers, plasticizers, antioxidants, colorants, and the like. The thickness of the walls of the housing may also impact the moisture permeability of the housing. A minimum thickness needed to achieve a particular degree of resistance to moisture transport will often depend on the material selected for the housing, as well as any additives.

Optionally, the housing 114 can be covered, in full or in part, with a coating. The coating can be provided to improve or alter one or more properties of the housing 114 including, for example, biocompatibility, hydrophobicity, moisture permeability, leaching of material into or out of the housing, and the like. In one embodiment, a coating can be applied which contains a compound, such as, for example, a drug, prodrug, hormone, or other bioactive molecule, that can be released over time when the stimulator is implanted. (In another embodiment, the housing itself may include such a compound to be released over time after implantation.)

In one embodiment, a conductor or conductors (not shown) couple the electrode(s) 154 on the distal portion of the lead 106 to the implantable pulse generator 102. The conductors can be formed using any conductive material. Examples of suitable materials include, for example, metals, alloys, conductive polymers, and conductive carbon. In one embodiment, the conductors are insulated by an insulating material. The insulating material may be any material that is a poor conductor of an electrical signal, including; for example, Teflon™, non-conductive polymers, or metal oxidation that is poor in electrical conductivity.

The body of the lead 106 may be made of any biocompatible material including, for example, silicone, polyurethane, polyetheretherketone (PEEK), epoxy, and the like. The lead body may be formed by any process including, for example, molding (including injection molding), casting and the like. In one embodiment, a method of making an array body is disclosed in U.S. patent application Ser. No. 11/319,291, which is incorporated herein by reference. The distal portion of the lead can have any shape including, for example, a circular, elliptical, square or rectangular shape. FIG. 1 illustrates a paddle lead but it will be recognized that other types of leads, such as percutaneous leads (for example, leads with ring electrodes) can be used.

Electrodes 154 are disposed on the array body. The electrodes 154 can be made using any conductive material. Examples of suitable materials include, for example, metals, alloys, conductive polymers, and conductive carbon. The number of electrodes 154 disposed on the array body may vary. For example, there can be two, three, four, five, six, seven, eight, nine, ten, eleven, twelve, thirteen, fourteen, fifteen, sixteen, or more electrodes 154. As will be recognized, other numbers of electrodes 154 may also be used.

Figure 6:
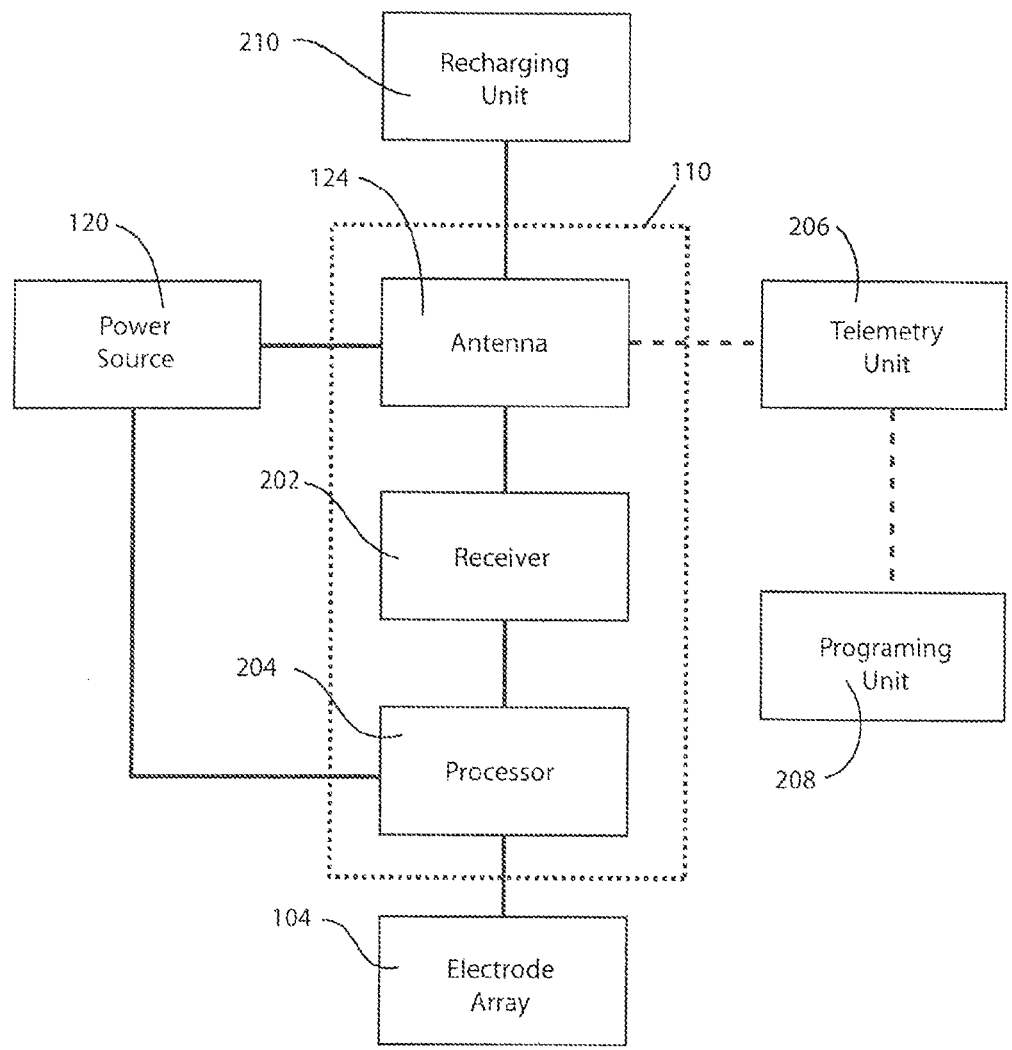
FIG. 6 is a schematic overview of components of a stimulation system, according to an embodiment of the invention.

FIG. 6 is a schematic overview of one embodiment of components of a stimulation system, including an electronic subassembly 110 (which may or may not include the power source 120), according to the invention. It will be understood that the stimulation system and the electronic subassembly 110 can include more, fewer, or different components and can have a variety of different configurations including those configurations disclosed in the stimulator references cited herein. Some or all of the components of the stimulation system can be positioned on one or more circuit boards or similar carriers within a housing of a stimulator, if desired.

Any power source 120 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 124 or a secondary antenna. The external power source can be in a device that is mounted on the skin of the user or in a unit that is provided near the stimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 6) external to the user.

In one embodiment, electrical current is emitted by the electrodes 154 to stimulate motor nerve fibers, muscle fibers, or other body tissues near the stimulator. The electronic subassembly 110 provides the electronics used to operate the stimulator and generate the electrical pulses at the electrodes 154 to produce stimulation of the body tissues. FIG. 6 illustrates one embodiment of components of the electronic subassembly and associated units.

In the illustrated embodiment, a processor 204 is generally included in the electronic subassembly 110 to control the timing and electrical characteristics of the stimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue. This process may be performed using an external programming unit, as described below, which is in communication with the processor 204.

Any processor can be used and can be as simple as an electronic device that produces pulses at a regular interval or the processor can be capable of receiving and interpreting instructions from an external programming unit 208 that allows modification of pulse characteristics. In the illustrated embodiment in FIG. 6, the processor 204 is coupled to a receiver 202 which, in turn, is coupled to the optional antenna 124. This allows the processor to receive instructions from an external source to direct the pulse characteristics and the selection of electrodes, if desired.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 110 does not include an antenna 124 or receiver 202 and the processor operates as programmed.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the housing.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A feed through interconnect assembly comprising:
an assembly frame having a first side and an opposing second side;
a plurality of feed through interconnects directly attached to the assembly frame, wherein a first set of the feed through interconnects extend inwardly, with respect to the assembly frame, from, and are directly attached to, the first side of the assembly frame, and wherein a second set of the feed through interconnects extend inwardly, with respect to the assembly frame, from, and are directly attached to the second side of the assembly frame, wherein the feed through interconnects and the assembly frame are made of a same conductive material;
a first contact pad and a second contact pad disposed on at least one of the feed through interconnects; and
a tab formed on the first contact pad of at least one of the feed through interconnects.

2. The feed through interconnect assembly of claim 1, further comprising at least one brace formed along a portion of the assembly frame, the at least one brace coupling the assembly frame to at least one of the plurality of feed through interconnects.

3. The feed through interconnect assembly of claim 2, wherein the at least one brace is removable from the assembly frame.

4. The feed through interconnect assembly of claim 1, further comprising a first brace that couples at least one feed through interconnect of the first set of the feed through interconnects to the assembly frame.

5. The feed through interconnect assembly of claim 4, further comprising a second brace that is different from the first brace and couples at least one feed through interconnect of the second set of the feed through interconnects to the assembly frame.

6. The feed through interconnect assembly of claim 1, wherein the first contact pad defines a coupling aperture having a first edge and an opposing second edge.

7. The feed through interconnect assembly of claim 6, wherein the tab has a proximal end and an opposing distal end, and wherein the tab is at least partially disposed within the coupling aperture with the proximal end of the tab attached to the first edge of the coupling aperture.

8. The feed through interconnect assembly of claim 6, wherein the coupling aperture is configured and arranged to receive a feedthrough pin extending from a sealed chamber of an implantable pulse generator.

9. The feed through interconnect assembly of claim 1, wherein the tab is configured and arranged to flex away from the first contact pad.

10. The feed through interconnect assembly of claim 1, further comprising at least one indexing hole defined in the assembly frame and extending entirely through the assembly frame.

11. The feed through interconnect assembly of claim 1, wherein the first contact pad and the second contact pad are disposed on each of the plurality of feed through interconnects.

12. The feed through interconnect assembly of claim 1, wherein the assembly frame is removable from the feed through interconnect assembly.

13. The feed through interconnect assembly of claim 1, wherein the plurality of feed through interconnects are spaced apart from one another at substantially uniform distances.

14. The feed through interconnect assembly of claim 1, wherein the plurality of feed through interconnects are interleaved.

15. The feed through interconnect assembly of claim 1, wherein the plurality of feed through interconnects extend from the assembly frame with the plurality of feed through interconnects extending along a plane of the assembly frame.

16. The feed through interconnect assembly of claim 1, wherein the plurality of feed through interconnects extend from the assembly frame with the plurality of feed through interconnects extending above or below a plane of the assembly frame.

17. The feed through interconnect assembly of claim 1, wherein the conductive material is selected from stainless steel material, platinum, platinum/iridium, or titanium.

* * * * *